United States Patent [19]
Chao

[11] Patent Number: 5,332,578
[45] Date of Patent: *Jul. 26, 1994

[54] PLATELET MEMBRANE MICROPARTICLES

[75] Inventor: Francis Chao, Newton, Mass.

[73] Assignee: PRP, Inc., Watertown, Mass.

[*] Notice: The portion of the term of this patent subsequent to Aug. 7, 2010 has been disclaimed.

[21] Appl. No.: 905,152

[22] Filed: Jun. 25, 1992

Related U.S. Application Data

[63] Continuation of Ser. No. 508,832, Apr. 12, 1990, abandoned, which is a continuation-in-part of Ser. No. 337,916, Apr. 14, 1989, Pat. No. 5,185,160.

[51] Int. Cl.$^5$ .................. A61K 35/14; C12N 7/04
[52] U.S. Cl. .................. 424/532; 424/529; 435/236
[58] Field of Search .................. 435/236; 424/101, 532

[56] References Cited

U.S. PATENT DOCUMENTS

| | | | |
|---|---|---|---|
| 4,456,590 | 6/1984 | Rubinstein | 514/2 |
| 4,540,573 | 9/1985 | Neurath et al. | 424/101 |
| 4,731,053 | 3/1988 | Hoffman | 604/89 |
| 4,753,797 | 6/1988 | Garcez | 424/532 |
| 4,760,131 | 7/1988 | Sundsmo et al. | 424/101 |
| 4,764,463 | 8/1988 | Mason et al. | 424/101 |
| 4,871,488 | 10/1989 | Mannino et al. | 264/4.6 |
| 4,994,438 | 2/1991 | Rubinstein | 424/530 |
| 5,185,160 | 2/1993 | Chao | 424/532 |

OTHER PUBLICATIONS

George et al., Biol. Abstracts, vol. 82:69920 (1986).
Schilt, U. Overview of Viruses Relevant to Blood Transfusion, "Virus Inactivation in Plasma Products".
Heimburger, N., and Karges, H. E., Strategies to Produce Virus-safe Blood Derivates. "Virus Inactivation in Plasma Products".
Piszkiewicz, D. Thomas, W. Lieu, M. Y., Tse, D., and Sarno, L., Virus Inactivation by Heat Treatment of Lyophilized Coagulation Factor Concentrates, "Inactivation in Plasma Products".
Winkelman, L., Fedlman, P. A., and Evans, D. R., Severe Heat Treatment of Lyophilised Coagulation Factors, "Virus Inactivation Plasma Products".
McGill, M., Vittorio, N., Fugman, D., Transfusion (Abstraction Edition; the 36th AABB Annual Meeting), 1983, p. 414 (Abstr.).
McGill, M., Fugman, D. A., Vittorio, N., Darrow, C., Platelet Membrane Vesicles Reduced Microvascular Bleeding Times in Thrombocytopenic Rabbits, J. Lab. Clin. Clin. Med. 109;127, 1987.
Klein, E., Farber, S., Djersasi, I., Toch, R., Freeman, G., Arnold, P., The Preparation of and Clinical Administration of Lypholized Platelet Material to Children with Acute Leukemia and Aplastic Anemia, J. Pediatrict 49:517, 1956.
Alkjaersig, N., Abe, T., and Seeger, W. H., Purification and Quantitative Determination of Platelet Factor 3, Journal Unknown, May 1955.
Wu, V-Y, McCoy, L. E., Platelet Factor 3: Quantitation and Characterization, Thromb. Res. 11:581, 1977.
Sandberg, H., Andersson, L-O, Hoglund, S., Isolation and Characterization of Lipid-Protein Particles Containing Platelet Factor 3 Released from Human Platelets, BioChem J., 203, pp. 303-311 (1982).
Sandberg, H., Gellerbring, A-K, Anderson, L-O, Determination of Platelet Factor 3 in Whole Blood by a Chromogenic Peptide Substrate Assay, Thromb. Res. 18:871, 1980.
Nichols, W. L., Kaese S. E., Moore, S. E., Blood (68 (Suppl. 1): 300a (abstr.), 1986.
Tullis, J. L., Surgenor, D. M., Baudanza, P., Preserved Platelets: Their Preparation, Storage and Clinical Use, Blood 14:459, 1959.
Chao, F. C., Tullis, J. L., Alper, C. A., Glynne, R. J., Silbert, S. E., Alteration in Plasma Proteins and Platelet Functions with Aging and Cigarette Smoking in Healthy Men, Thrombos Haemostas, 47:459 1982.
Chao, F. C., Tullis, J. L., Tinch, R. J., Conneely, G. S., Baudanza, P. Platelet Phoresis by Discontinuous Centrification: Effective Collecting, Brit J. Haematol, 39:177, 1978.
Kahn, R. A., Allen, R. W., Baldassare, J., Alternate Sources and Substitutes for Therapeutic Blood Components, Blood 66:1, 1985.
Hjort, P. F., Perman, V., Cronkite, E. P., Fresh, Disintegrated Platelets in Radiation Thrombocytopenia:

(List continued on next page.)

Primary Examiner—Douglas W. Robinson
Assistant Examiner—Deborah K. Ware
Attorney, Agent, or Firm—Wolf, Greenfield & Sacks

[57] ABSTRACT

A heat-treated, viral-inactivated platelet membrane microparticle product is provided. The microparticles may be prepared from outdated mammalian platelets. The microparticle product contains isolated platelet membrane fragments that are free of alloantigens and GP IIb/IIIa complexes further, the product may be used as a pharmaceutical preparation in transfusions.

14 Claims, 4 Drawing Sheets

OTHER PUBLICATIONS

Correction of Prothrombin Consumption Without Correction of Bleeding, Proc. Soc. Expt. Biol Med. 102:31, 1959.

Firkin, B. G., Arimura, G., Harrington, W. J.: A Method for Evaluation the Hemostatic Effect of Various Agents in Thrombocytopenic Rats and Mice, Blood 15:388, 1960.

Jackson, D. P., Soronson, D. K., Cronkite, E. P., Bond, V. P., and Fliedner, T. M., Effectiveness of Transfusions of Fresh and Lyophilized Platelets in Controlling Bleeding Due to Thrombocytopenia, J. Clin. Invest., 38:1689–1697 (1959).

Zucker, M. B., Can Platelet Fragments Induce Hemostasis?, J. Lab. Clin. Med. 109:111, 1987.

Stefanini, M., Kistner, S., Use of Platelet Derivatives and Platelet Substitutes in the Management of Thrombocytopenic States, Clinical Research Proceedings, 5: pp. 151–152 (1957) (Abst).

Walsh, P. N., Schmaier, A. H., Platelet—Coagulant Protein Interactions, In Hemostatis and Thrombosis (Colman R. W., Hirsh J., Marder V. J., Salzman E. W., Eds), Kippincott, N.Y. 1987, p. 689.

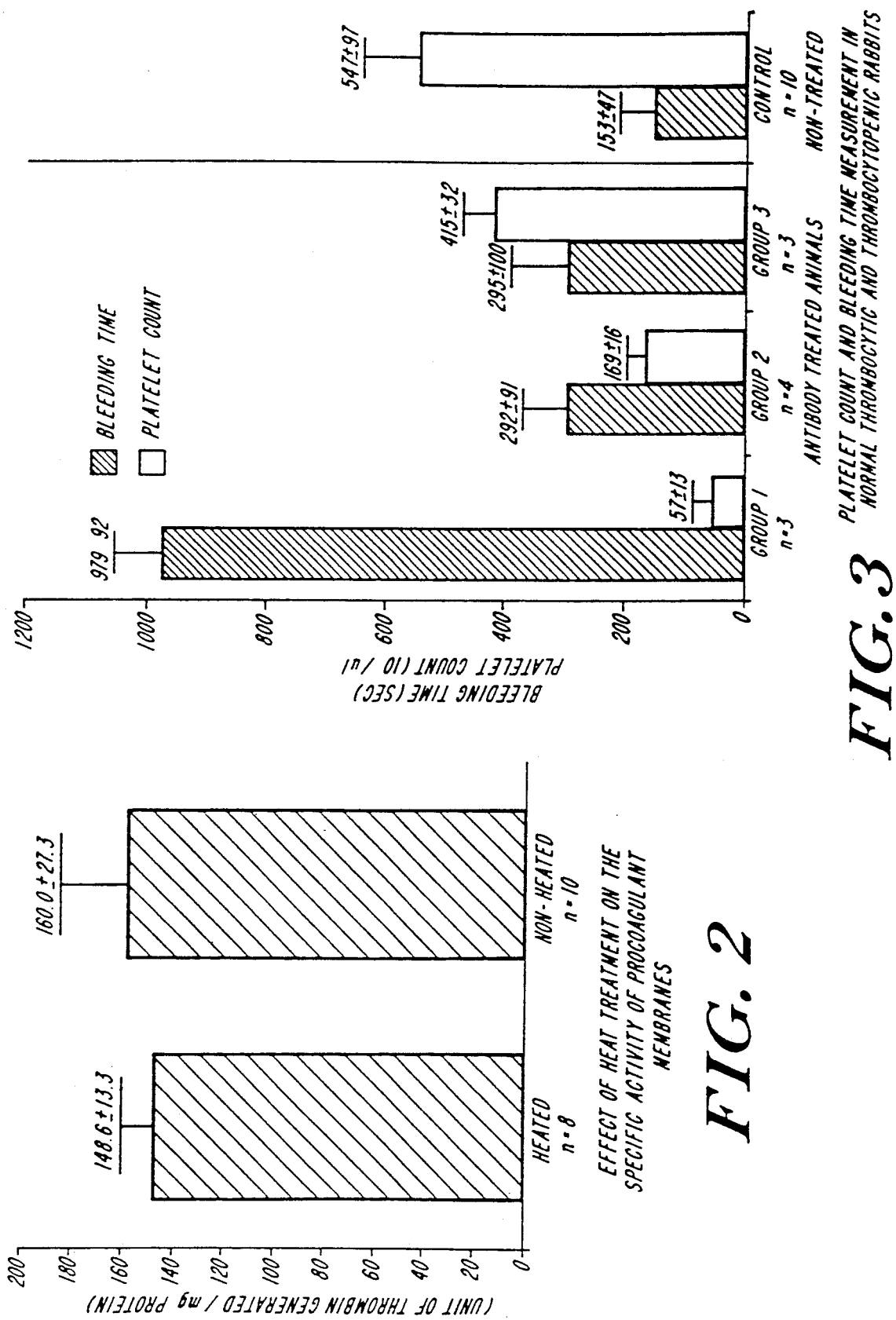

PLATELET MEMBRANE MICROPARTICLES

This application is a continuation of application Ser. No. 07/508,832, filed Apr. 12, 1990, now abandoned which is a continuation-in-part of application Ser. No. 07/337,916, filed Apr. 14, 1989, now U.S. Pat. No. 5,185,160, the disclosure of which is incorporated herein by reference.

FIELD OF THE INVENTION

This invention relates generally to the field of medicine and more particularly to a platelet membrane microparticle preparation for use in transfusions to control bleeding.

BACKGROUND OF THE INVENTION

The body of a normal adult contains 4.0 to 5.5 liters of blood, composed of approximately 60% fluid (plasma) and 40% formed elements (red cells; white cells; and platelets). Under normal physiological conditions, the main function of the platelets is prevention of hemorrhage (bleeding).

Platelets are formed in the bone marrow from precursor cells called megakaryocytes and have a life span of 8 to 10 days in circulation. As a consequence of this short life span, platelet deficiency occurs rapidly when the ability of the bone marrow to produce platelets is depressed, such as in cancer patients undergoing chemotherapy. Platelet deficiency also may occur as a result of various diseases, for example when antibodies are produced in vivo against platelet surface glycoproteins or against other platelet surface antigens. Such depletion or destruction of platelets results in an insufficient quantity of circulating platelets (a condition referred to as thrombocytopenia) and can cause uncontrolled bleeding. Platelet deficiency also may result from surgery involving for example extracorporeal circulation which tends to damage or destroy circulating platelets. Clinical management of thrombocytopenia typically has involved transfusion of fresh, intact platelets.

It is predominantly held that only metabolically-active, intact platelets can function in vivo to arrest bleeding. As a consequence, transfusion therapy has been dependent on the procurement of high quality, fresh, viable platelets. Platelets for transfusion typically are prepared: (a) from freshly donated blood units, called random-donor platelets or (b) from a single donor by apheresis, called single-donor platelets. These transfusion products are plasma suspensions of fresh, concentrated, intact platelets.

A major drawback of the current practice of platelet transfusion is the short shelf life of intact platelets, three to five days. Many platelet units collected by hospitals, bloodbanks and the like unfortunately are discarded due to outdating. Because of their short shelf life, it is very difficult to maintain large inventories of platelet units. This problem is particularly critical in connection with decentralized operations, such as the military, civil defense and disaster agencies.

Several substitutes for intact, viable platelets have been attempted for transfusion both clinically and in animal models. In 1956 (1), it was reported that hemostasis was achieved following the clinical administration of lyophilized platelets, suggesting that the morphological integrity of platelets may not be essential for the retention of at least some of the in vivo functions of intact platelets. A major side effect of the intravenous administration of the lyophilized platelet material was that the patient experienced severe pain at the site of infusion, possibly due to vasospasm caused by the high serotonin content in the lyophilized material. Contrary to the foregoing result, it was reported in 1959 (2) that fresh, ultrasound-disrupted whole platelet preparations failed to reduce the number of erythrocytes in the lymph of thrombocytopenic dogs. More recently, McGill et al (3) reported that the transfusion of platelet membrane concentrates shortened bleeding times in thrombocytopenic rabbits. The concentrate included ghost platelets about the size of a normal platelet and containing mitochondria and remnants of the surface-connecting system. McGill's concentrate was prepared by: (1) centrifuging the whole blood of rabbits to pellet fresh platelets; (2) freezing the pellet at $-65°$ C.; (3) thawing and then twice--freezing and thawing the pellet; and (4) rinsing and resuspending the pellet in platelet-free plasma.

In preparing the foregoing platelet membrane fractions, temperature conditions of about 4° C. or below were maintained. Such temperatures are standard when working with biologicals as activity is routinely lost in very short intervals when biologicals are exposed to higher temperatures. For example, proteins such as enzymes may be inactivated by heating them to about 60° C. Activity may be lost even at 4° C. For example, it has been reported that partially purified platelet factor 3 (PF-3) loses a major portion of its clotting activity after five days storage at 4° C. (4). (PF-3 appears to be associated with a platelet membrane complex that provides a catalytic surface to promote thrombin generation.) Such loss of activity is of great concern when considering the use of a platelet fraction as a pharmaceutical.

When preparing a platelet fraction for use in humans, it is of course necessary to use sterile conditions. Like whole blood transfusions, the use of donated platelet units exposes the recipients to the risk of transmission of diseases such as AIDS, hepatitis, and other transfusion-related diseases. Another risk is that after multiple transfusions, the recipient/patients may develop antibodies against donated platelets (a condition known as alloimmunization). Such antibodies can cause rapid destruction of the platelets transfused. Further, bacterial contamination of stored platelets is a significant hazard in transfusions.

SUMMARY OF THE INVENTION

The invention provides pharmaceutical and diagnostic products derived according to novel methods from platelet membranes. The products include platelet membrane fragment preparations that have procoagulant activity and that may be used as transfusion substitutes for whole platelets to control bleeding, may be used topically to promote wound healing or may be used as a diagnostic agent in vitro or in in vivo.

According to one aspect of the invention, the platelet membrane fragment preparation is free of active virus. The preferred method for making this preparation involves heat-treating a platelet membrane fragment preparation to reduce or eliminate viral contamination, as well as bacterial contamination. Although the preparation is heat-treated, surprisingly, it retains its procoagulant and hemostatic properties. Moreover, the heat-treated membrane fragment is far more stable than expected. The preparation is capable of being stored in solution at 4° C. for at least eight weeks without significant loss of procoagulant activity for at least six months (greater than 90% retained). It retains this activity (greater than 90%) even after lyophilization. In addition the protein and phospholipid content do not change after lyophilization and storage for six months.

According to another aspect of the invention, the preparation is nonimmunogenic, and in particular is nonantigenic with respect to class I HLA antigenic determinants. Thus, the suitability of the preparation for a particular recipient is not limited by the genetic characteristics of the donor.

According to yet another aspect of the invention, the platelet membrane fragment preparation, which has procoagulant activity and is capable of controlling bleeding, is substantially free of GP IIb/IIIa complex. This is surprising in view of the widely held belief that GP IIb/IIIa complex is involved in and necessary for hemostasis.

The platelet membrane fragment preparation preferably is substantially free of ghost platelets, and contains relatively homogeneous microparticles. Preferably, at least 80% of the microparticles have a diameter less than 600 nanometers, and at least 95% have a diameter less than one micron. Most preferably, the microvesicles have an average diameter of between about 300 and 400 nanometers. Such microparticles are about 1/5 to 1/7 the size of a typical ghost platelet.

The preferred preparation contains virtually no serotonin (less than 0.02% of that found in platelet lysates), thereby eliminating the respiratory and vascular problems characteristic when certain of the preparations of the prior art are used for transfusion. The preparation further has no detectable purine nucleoside phosphorylase activity, a cytoplasmic enzyme marker, and is substantially free of factors V, VIII, IX and X. In one embodiment the microparticle fraction has 3% carbohydrate, 30% phospholipid, 58% protein and 9% cholesterol by weight and the ratio of protein versus phospholipid is $1.97 \pm 0.10$ (mean $\pm$ SD, n=7).

Surprisingly, the platelet membrane fragment preparation may be prepared from outdated platelets. Typically, hospitals and the like store platelets for transfusion at room temperature for three to five days. After this, the platelets are considered unusable and are discarded as "outdated platelets". It has been discovered that the pharmaceuticals and diagnostics of the invention may be prepared from such outdated platelets. Thus, the invention has as an advantage the provision of a platelet membrane fraction for transfusion prepared wholly or in part from outdated platelets, thereby making use of huge quantities of platelets heretofore discarded as useless.

Methods for preparing the platelet derived products of the invention also are provided. In one aspect of the invention, a preparation containing platelets or platelet membrane fragments having prothrombinase activity is treated under conditions sufficient to inactivate any virus contained in the preparation. Preferably, the preparation is heat-treated. Such a preparation also may be homogenized, preferably by sonocation, to form platelet membrane microparticles substantially free of ghost platelets. The preparation also may be treated to remove substantially all GP IIb/IIIa, a surface glycoprotein complex.

The invention also provides a method for preparing a platelet derived product using outdated platelets or membrane fragments thereof as the starting material. The outdated platelets may be from a single donor source, or may be pooled from multiple sources. This method also may include treatment for inactivating virus, treatment for forming microparticles and treatment to substantially eliminate GP IIa/IIIa.

The most preferred method for preparing the products of the invention involves repeated freeze-thawing and washing platelets to yield primarily ghost platelets and a lysate. The ghost platelets then are separated from the lysate and are suspended in a solution to form a suspension. Then the suspension containing the ghost platelets is heated to at least 60° C. for at least two hours to inactivate viral contaminants. The heat treatment also causes a precipitate to form. However, The precipitate is not removed at this point because it contains a significant amount of the desired activity. Instead, the suspension including the precipitate first is homogenized, preferably by sonication, and then the precipitate is separated from the suspension. The suspension then may be stored or used for transfusion.

The platelet membrane fragment preparation may be used in pharmaceutically effective amounts in the treatment of animals or humans to prevent bleeding. When used as a pharmaceutical preparation for transfusions, the sterile preparation may be suspended in any physiologically compatible solution such as saline or plasma. It may be used alone, or with other agents, including whole platelets. The preparation is an ideal additive to artificial blood. The preparation also may be applied topically to stop bleeding and to treat wounds. In this regard the preparation may be suspended in a pharmaceutically acceptable carrier such as a gel or ointment or may be impregnated in a carrier such as gauze. The preparation also may be used as a carrier for drug delivery, or may be labeled and used diagnostically, for example, as an imaging agent to trace the location of a clot.

BRIEF DESCRIPTION OF THE DRAWINGS

FIG. 2 is a graph showing the effect of heat treatment on PF-3 specific activity;

FIG. 3 is a graph showing the platelet count and bleeding time in normal thrombocytic and thrombocytopenic rabbits;

DETAILED DESCRIPTION OF THE PREFERRED EMBODIMENTS

Figure 1:
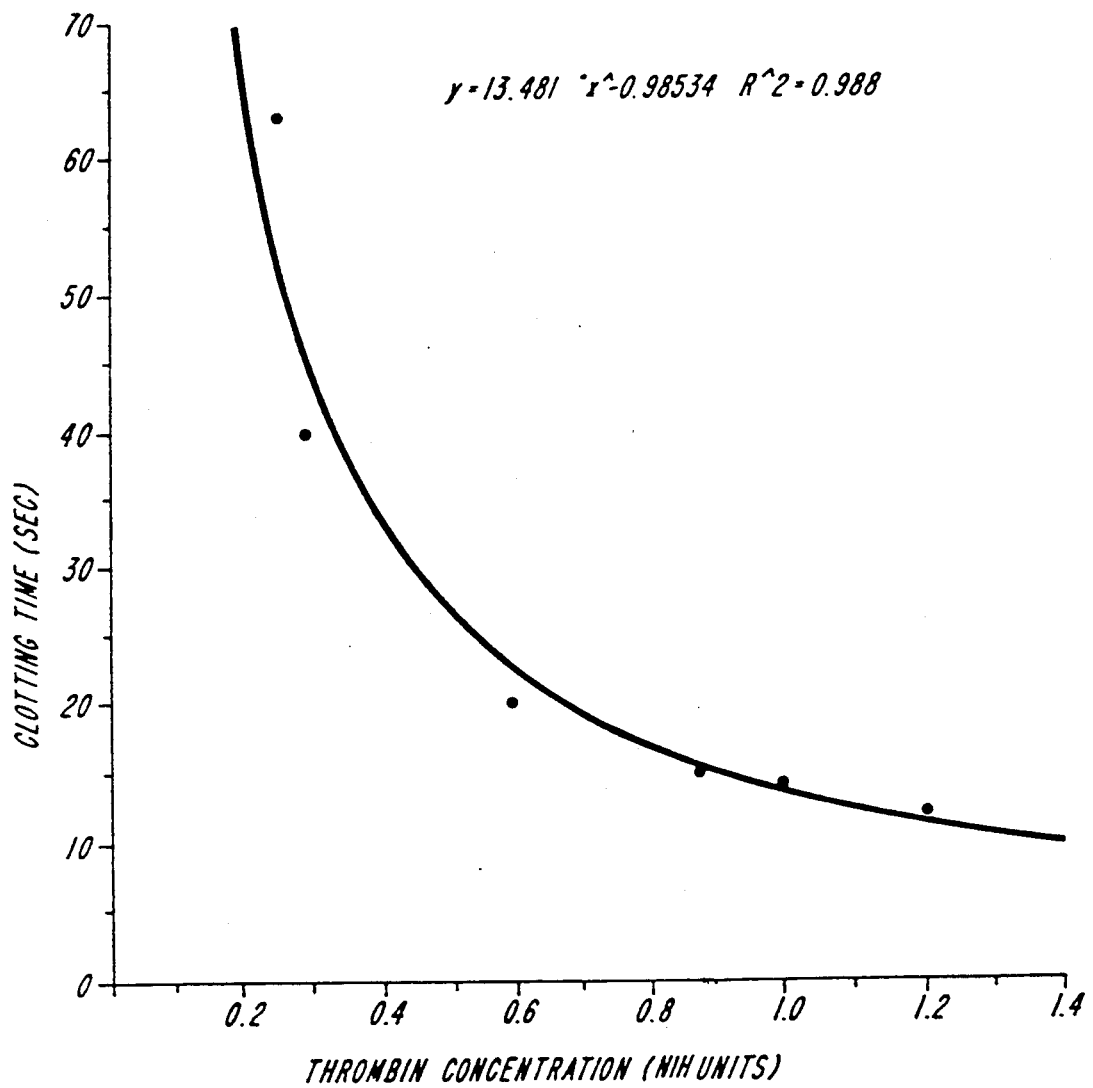
FIG. 1 is a graph showing a standard curve for thrombin clotting time.

The products of the invention are prepared from whole platelets or from membrane derivatives of whole platelets. The whole platelets may be freshly collected platelets or may be outdated platelets. By outdated platelets it is meant platelets that have been stored at a temperature of between about 4° C. and room temperature for at least three days. Outdated platelets are those which according to accepted practice are discarded as being no longer suitable for use as a transfusion material. Derivatives of platelets means non-intact platelets such as ghost platelets or platelet membrane fragments including platelet membrane microvesicles.

The products of the invention are administered to subjects in effective amounts. The term "subject" is intended to include living organisms having a hemostatic capability mediated at least in part by platelets, e.g. humans, dogs, cats, horses and the like. An "effective amount" is that amount capable of achieving the particular therapeutic or diagnostic purpose for which the product is administered. In the general case of transfusion, an effective amount is that which will act to restore the hemostatic function to substantially the same level that would be achieved if whole platelets were transfused. In the case of a subject suffering from thrombocytopenia, an effective amount is that amount which is capable of reducing the bleeding time in the subject, preferably to non-dangerous levels and most preferably to levels consistent with normal individuals. An effective amount can be determined on an individual basis and will be based, at least in part, upon the subject's size, the severity of the symptoms to be treated and the results sought. Thus, an effective amount can be determined by one of ordinary skill in the art employing such factors and using no more than routine experimentation.

The products of the invention may be treated such that they are free of active virus. Free of active virus means that the product has been subjected to conditions sufficient to inactivate or destroy any virus present, such as for example HBV, NANBHV, CMV or HIV. Such conditions include those treatments involving antibodies, ethanol, ultraviolet light, organic solvent-detergent and phenanthroline chelating agents. (See "Virus Inactivation in Plasma Products", Ed.J.-J. Morgenthaler, *Current Studies in Hemotology and Blood Transfusion,* No. 56, Karger, N.Y. 1989, expressly incorporated herein by reference.) The preferred method of viral inactivation includes heat treatment for a duration and extent to inactivate or destroy virus.

The products of the invention also may be treated so as to reduce or eliminate their immunogenicity when transfused. The products of the invention adventageously are prepared from pooled platelets, which ordinarily would induce an antibody response when transfused into most individuals. Currently, alloimmunization is a difficult problem in the management of thrombocytopenic patients who require repeated platelet transfusion. Platelets exhibit HLA-A and HLA-B antigens which either are a part of platelet membranes or are absorbed from plasma. The development of antibodies against HLA-A or HLA-B (which is the primary cause of platelet alloimmunization) causes rapid destruction of transfused platelets, thus diminishing the effect of transfusion of platelets on hemostasis. Contamination by white cells (which are a ready source of HLA antigens) in platelet concentrates also may contribute to the development of alloimmunization.

The preferred products of the invention are nonimmunogenic, nonalloimmunogenic and nonimmunogenic to HLA determinants (particularly Class I HLA determinants). Nonimmunogenic herein means that a subject, after several transfusions, does not mount an immunological response sufficient to interfere with the therapeutic effect of the transfused product. Nonalloimmunogenic herein means that a subject, after several transfusions of material prepared from alloimmunogenic sources, does not exhibit a detectable immunological response against alloantigens. By detectable, it is meant that serum antibody against alloantigens cannot be detected using conventional techniques such as dot assays or that the immunological response to any alloantigens is not sufficient to interfere with the therapeutic effect of the transfused product.

The preferred method for preparing the preferred product of the invention is as follows. Freshly-collected, stored (one to five days at 20°-25° C.) or outdated (beyond five days at 4° C.) platelet concentrates (50-60 ml/concentrate) were pooled in 600 ml blood bags (Fenwall transfer pack unit, 4R2023, Fenwall Laboratories, Deerfield, Illinois) via sterile plasma transfer sets (Fenwall 4C2243, Fenwall Laboratories, supra). Each bag contained a total of 500-600 ml of platelet concentrates (hereinafter, 600 ml unit). The 600 ml units were centrifuged at 1,000 rpm for 11 minutes at 22° C. to remove contaminating red and white blood cells (PR7000, International Equipment Company, Needham Heights, Mass.). The supernatants, which contained the platelets, then were transferred to new 600 ml blood bags and centrifuged at 3,000 rpm for 25 minutes at 22° C. to separate platelets from plasma. Platelet-poor plasma was expressed and each of the resulting platelet pellets was gently resuspended in 20 ml of an 0.9% MaCl solution (physiological saline), diluted to a final volume of 100 ml with additional saline, and then pooled in 300 ml blood bags (three 100 ml samples per bag corresponding to three original 600 ml units). The resuspended platelets again were pelleted by centrifugation at 3,000 rpm for 20 minutes at 22° C. The supernatant was removed and the platelet pellet was washed twice with physiological saline by repeated resuspension and centrifugation.

The washed platelets were finally resuspended in physiological saline (25 ml per each 600 ml unit) and disrupted by repeated freezing (at $-80°$ C. for at least six hours) and thawing (at 25° C. for at least one hour), three times. The frozen and thawed suspension was diluted with physiological saline (100 ml per each 600 ml unit) and centrifuged at 3,000 rpm for 30 minutes to collect a platelet ghost pellet. This platelet ghost pellet was resuspended in physiological saline (100 ml per each 600 ml unit) and washed twice by repeated resuspension and centrifugation.

Other methods may be employed to disrupt platelet membranes and to isolate a platelet ghost fraction. For example, platelets may be equilibrated with glycerol and then may be broken hypotonically by rapid dilution of the glycerol concentration external to the cell. This creates an osmotic pressure gradient across the external membrane of the platelets, which leads to a rupture of the cell membrane. In addition, many other chemical agents (e.g., NaCl) may be used in a similar manner to induce osmotic shock and disrupt platelets. According to the preferred embodiment, repeated freezing and thawing was used.

The washed ghost pellet was resuspended in physiological saline (40-50 ml per each 600 ml unit) and heated at 60° C. for 20 hours in a water bath. Alternatively, the platelet ghost suspension may be heated to 100° C. for five minutes. These conditions are sufficient to inactivate any viral contaminants. A gross precipitate developed during the heat treatment. This heat-treated, platelet ghost suspension then was homogenized in a sonicator (ultrasonic processor Model W-385, Heat Systems, Inc., Farmingdale, New York) using a $\frac{1}{2}''$ disruptor horn in a flow cell (Model 800B, Heat Systems). The sonicator system was flushed first with nitrogen prior to injection of the platelet ghost suspension. The suspension was sonicated by pulsing at 20 kHz for 5 minutes and 43 seconds (2 second cycle, 1.4 seconds on, 0.6 seconds off) with output control setting at "4" to produce double amplitude of 48 micrometers. The sonicated preparation next was centrifuged at 3,000 rpm for 30 minutes at 22° C. to separate the precipitated material from the formed platelet membrane microparticles which remain in the supernatant. The supernatant was removed and stored in sealed containers at either 4° C., −20° C. or −80° C. under nitrogen, or stored lyophilized under nitrogen. Unless otherwise indicated, microparticles stored at 4° C. were used in the following procedures.

The platelet microparticle fraction prepared as described above was free of active virus. It also was substantially free of platelet ghosts, with greater than 80% of the microparticles being less than 600 nanometers in diameter and greater than 95% less than 1,000 nanometers. The average diameter of the microparticles prepared from newly outdated platelets (within two weeks after outdating) for 7 different preparations was between 300 and 400 nanometers. The mean diameter for the 7 preparations was 341 nanometers.

The platelet microparticle fraction also was substantially free of serotonin, GPIIb/IIIa (a surface glycoprotein), purine nucleoside phosphorylase, coagulation factors V, VIII, IX and X, and thrombospondin (an alpha granule component). On the other hand, GPIb (another surface glycoprotein) was present and Beta-glucuronidase (a lyzosomal marker) also was detectable (about 25% as a percent of lysate). The absence of GPIIb/IIIa was surprising since it is believed that GPIIb/IIIa is necessary for hemostasis.

The composition of the platelet microparticle fraction was determined in two different sets of experiments for certain components and is presented in Table I:

TABLE I

| | PERCENT OF COMBINED WEIGHT (W/W) | | | |
|---|---|---|---|---|
| EXPT. | CARBO-HYDRATE | PHOSPHO-LIPID | PROTEIN | CHOLES-TEROL |
| N = 4 | 3.3 ± 0.14 | 30. ± 0.9 | 57.8 ± 0.9 | 9 (assumed) |
| N = 8 | 2.6 ± .3 | 30.1 ± 2.5 | 53.2 ± 1.7 | 9.9 ± .9 |

The procoagulant activity of the preferred platelet microparticle fraction prepared from newly outdated platelets was determined using the Russel's viper venom time (5) which is used to measure PF-3 activity. The Russel assay is a thrombin generation test, for which the end point may be determined by fibrinogen clotting. The specific activity was determined by comparison to a thrombin standard curve and may be expressed as units (U) of thrombin generated per mg of platelet protein or per mg of platelet phospholipid. The PF-3 specific activity per mg protein (U/mg) was determined in a first set of experiments to be $148.1 \pm 13.4$ (n=7). In a second set of experiments it was $175 \pm 8$ (n=8). The PF-3 specific activity per mg phospholipid (U/mg) in the first set of experiments was $291.3 \pm 40.0$. In the second set of experiments it was $310 \pm 23$. These specific activities far exceed those for fresh, intact whole platelets. It is believed that this is due to the release of procoagulant membrane fragments normally unavailable in intact platelets.

The specific activity was retained even after lyophilization, although it was necessary to add a protective material to the preparation to retain greater than about 60% of the specific activity (sucrose at 0.4 gm/dl, >90% activity retained.)

The composition of the phospholipid portion of the preparation was determined in two different sets of experiments and is shown in Table II:

TABLE II

| PERCENT OF COMBINED PHOSPHOLIPID (W/W) | | | | | |
|---|---|---|---|---|---|
| EXP. | PI | PS | PE | PC | SP |
| N = 4 | 5.8 ± 1.0 | 10.1 ± 0.9 | 22.5 ± 1.5 | 45.8 ± 4.0 | 15.4 ± .7 |
| N = 8 | 6.8 ± .5 | 12.2 ± .7 | 23.8 ± 2.1 | 40.6 ± 2.3 | 16.6 ± 1.5 |

PI: phosphatidylinositol
PE: phosphatidylethanolamine
SP: sphingomyelin
PS: phosphatidylserine
PC: phosphatidylcholine Platelet microparticle fractions were tested for their procoagulant activity and for their ability to control bleeding in thrombocytopenic animals. The procoagulant activity of a microparticle fraction prepared from newly outdated platelets was found to be comparable to one prepared from fresh platelets. Fractions prepared from fresh and newly outdated platelets had comparable procoagulant activity to whole platelets. The transfusion of this fraction shortened bleeding time in all recipient animals.

The effect of heat treatment and the effect of sonication on procoagulant activity also was tested. The microparticle fraction prepared from newly outdated platelets was found to be relatively stable to heat treatment. It further was discovered that the procoagulant activity of this platelet microparticle fraction was diminished greatly when homogenization preceded heat treatment. These and other properties of the microparticle fractions of the invention are set forth more fully in the examples below.

The product prepared according to the above-identified procedure, as well as various intermediates, were tested in immunological dot assays for the presence of GPIIb/IIIa. GPIIb/IIIa was present in the intact platelet preparations, the platelet lysate, the supernatant from the platelet lysate, and the platelet membrane ghost fraction. There was no detectable GPIIb/IIIa in a heated platelet membrane ghost fraction or in the final product.

The final product and intermediates also were tested in immunological dot assays for the presence of HLA antigens (Class I). HLA antigens were present in the washed, intact platelet preparations, the platelet lysate, the supernatant from the platelet lysate, and the platelet membrane ghost fraction. HLA antigens were not detectable in a heated platelet membrane ghost fraction or in the final product.

The final product and various intermediates further were tested in immunological dot assays for the presence of GPIb. All samples tested, including those heat treated, showed the presence of GPIb.

The foregoing description is of a preferred embodiment. The invention in its broadest sense, however, is not so limited. One aspect of the invention is the provision of platelets or a platelet membrane fraction heat-treated to eliminate viral contaminants. While such heat treatment is known to inactivate viral contaminants generally, it never has been used in connection with a platelet preparation. The invention therefore provides for the first time a viral-inactivated, platelet fraction useful for transfusion.

Another aspect of the invention is a transfusion preparation which has been prepared from outdated platelets. The invention for the very first time makes the great quantities of outdated platelets, ordinarily discarded, useful for transfusion. Moreover, because there is an increasing potential for viral contamination of outdated platelets during storage, the heat treatment step of the invention also contributes to making outdated platelets useful by ensuring that they are viral-inactivated.

The invention also combines heat-inactivation with a homogenization step in preparing a platelet microparticle fraction substantially free of ghost platelets. The preparation contains microparticles of homogeneous size and substantially free of unwanted cytoplasmic material. According to a preferred method of the invention, the homogenization (sonication) follows the heat-inactivation step which results both in creating the microparticles of homogenous size and in preventing a substantial amount of the activity from being bound up in any precipitate formed during the heat-inactivation step.

As described above, the microparticle fraction may be prepared in stages. First, the platelet membrane was partially disrupted to form a ghost platelet fraction and a lysate containing cytoplasmic materials. Once the platelet ghosts are separated from this cytoplasmic material, then the ghost platelets are homogenized to form a fraction substantially free of ghost platelets and containing microparticles of substantially uniform size. It will be understood, however, that the preliminary stage of partial disruption may be eliminated altogether. Thus, platelets may be sonicated and the formed microparticles may be isolated from the lysate.

It is believed that the platelet membrane microparticle fraction of the invention is substantially nonimmunogenic when compared to whole platelets and therefore may be prepared from pooled platelets collected from various donors with matching blood groups. The extensive washing which effectively removes all white blood cells may also contribute to the nonimmunogencity of the preparation.

The preferred products of the invention thus have procoagulant activity, are free of virus, are nonalloimmunogenic and are stable such that they may be prepared, lyophilized and stored in commercial amounts in suitable containers.

EXAMPLE 1

PF-3 (platelet factor-3) procoagulant activity was measured by the Russel viper venom time assay, which is a thrombin generation test. The end point of the test is determined visually by the clotting of fibrinogen present in a pooled human plasma sample.

A stock solution of $CaCl_2$ (0.025 M in imidazol buffer, pH 7.3) was maintained at 37° C. Pooled human plasma and the platelet membrane microparticle fractions in solution (25 ug/ml in saline) were stored at room temperature. Russel viper venom (RVV; 10 ug/ml in saline; Wellcome Diagnostics, Dartford, England) was kept on ice.

The assay was initiated by mixing and incubating 0.1 ml each of pooled plasma and the solution of platelet membrane microparticles in a borosilicate glass tube (12×75 mm) at 37° C. for 5–10 minutes. RVV solution (0.1 ml) was then added and further incubated for 30 seconds at 37° C. followed by adding 0.1 ml of $CaCl_2$ solution. The time between the addition of $CaCl_2$ solution and the detection of fibrin clotting was determined. The unit of thrombin generated by the assay system was calculated from a standard curve of thrombin clotting time (FIG. 1) using purified bovine thrombin (Sigma 850-1; Sigma Chemical Co., St. Louis, Mo.) and pooled human plasma.

The effect of heat treatment and the effect of sonication on procoagulant activity (PF-3) using Russel's viper venom time (5) was tested. As illustrated in FIG. 2, heat treatment, followed by sonication, resulted in a platelet membrane microparticle fraction that retained a substantial amount of its procoagulant activity. However, when sonication preceded heat treatment (not shown), the procoagulant activity of the platelet membrane microparticle fraction was altered drastically, the procoagulant activity being reduced by 50%.

EXAMPLE 2

The platelet microparticles were tested for their ability to control bleeding in antibody-induced, thrombocytopenic animals. Anti-rabbit platelet antiserum was used to induce thrombocytopenia in rabbits. Platelet counts and bleeding time first were determined in 10 normal rabbits (body weight 3.53±0.41Kg; platelet count, 548,000±97,000/ul; bleeding time, 153±47 sec; mean±SD). Anti-rabbit platelet antiserum was obtained from a commercial source then was administered intravenously to the 10 rabbits at a dose of 0.2–0.4 ml antiserum per kg body weight. At two hours after antiserum injection, thrombocytopenia of varying degree was present in all animals. Data were grouped according to the degree of induced thrombocytopenia": GROUP 1, platelet count less than 80,000/ul; GROUP 2, platelet count between 100,000–200,000/ul and GROUP 3, platelet count above 200,000/ul (FIG. 3).

Prolongation of bleeding time also was induced in all 10 antiserum-treated rabbits (measured at two hours after antiserum injection). Marked prolongation occurred only in Group 1 animals (severe thrombocytopenia, <75,000/ul) and a moderate prolongation was observed in both Group 2 and 3 animals (FIG. 3).

Figure 4:
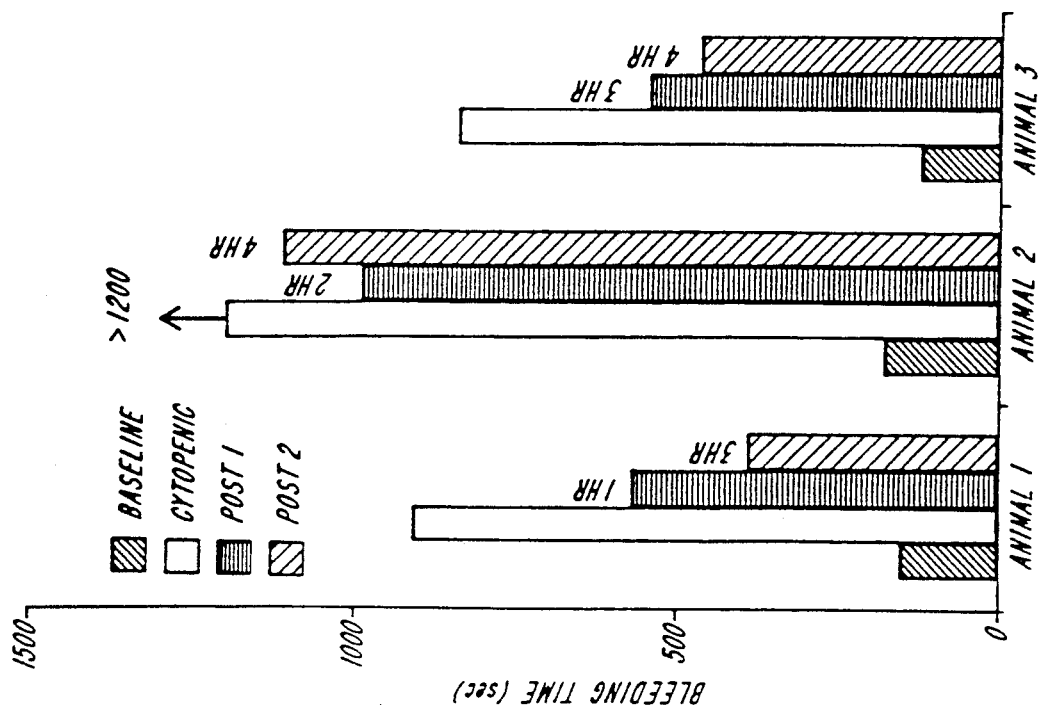
FIG. 4 is a graph showing the effect of transfused platelet membrane microparticles on the bleeding time in doxorubicin hydrochloride-induced thrombocytopenic animals.

Platelet microparticle fractions prepared from newly outdated platelets were transfused (2 mg protein/kg body weight) into Group 1 animals with severe thrombocytopenia. Referring to FIG. 4, platelet counts obtained at two hours after antiserum injection were 41,000, 73,000 and 56,000/ul for animals 1, 2 and 3, respectively. At the same interval, bleeding time was marked prolonged in all three rabbits, especially rabbit number 2, in which profuse bleeding from the test site persisted even at 20 minutes after the initial incision and required application of local pressure to stop the bleeding. After receiving the platelet microparticles, animals 1 and 3 showed progressive shortening of bleeding time, while spontaneous arrest of bleeding occurred within 20 minutes in rabbit number 2, without the need of local pressure. Thus, a general trend of shortening of bleeding time after transfusion of the platelet microparticles of the invention was demonstrated in all recipient animals.

EXAMPLE 3

The platelet microparticles were tested for their ability to control bleeding in Doxorubicin hydrochloride-induced, thrombocytopenic animals. Doxorubicin hydrochloride (Adriamycin; 2 mg/kg body weight) was administered intravenously to nine rabbits to induce thrombocytopenia. The baseline platelet count (before doxorubicin injection) was 488,000±94,000/ul. The baseline bleeding time was 128±21 sec. One week after doxorubicin injection, platelet count was reduced to 130,000±31,000/ul ($p<0.01$) with a 2.4 fold increase in bleeding time (311±89 sec; n=9) over the thrombocytopenic controls ($p<0.01$).

Figure 5:
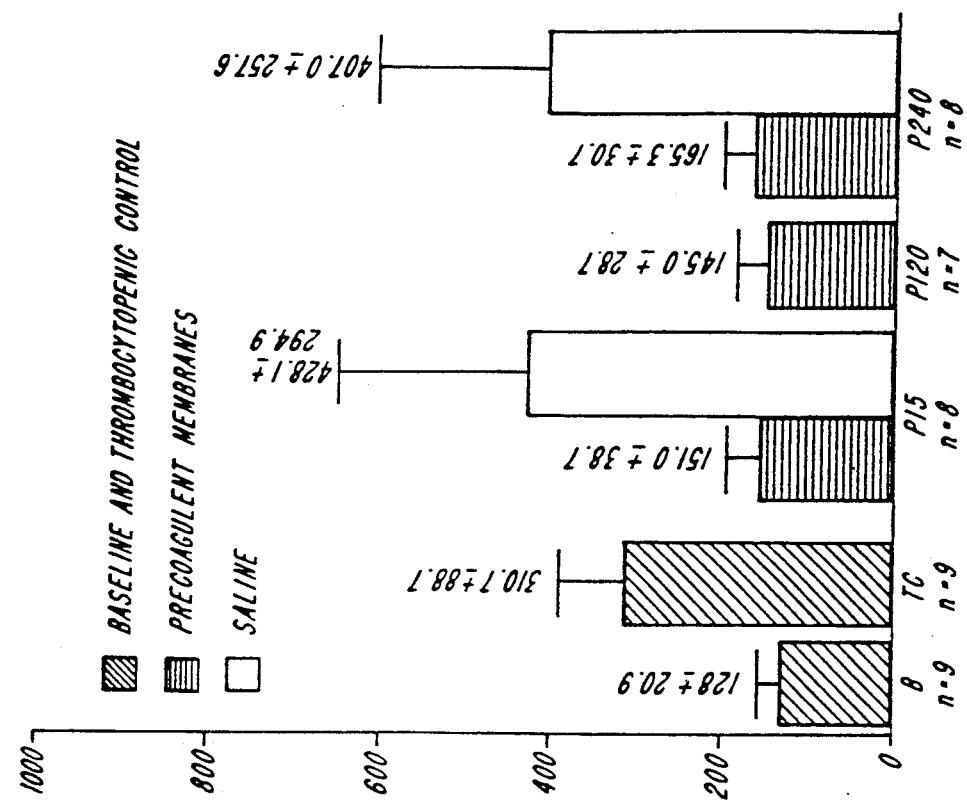
FIG. 5 is a graph showing the effect of transfused platelet membrane microparticles on antibody induced thrombocytopenic animals.

Platelet microparticle fractions (2 mg membrane protein/K9 body weight), prepared from newly outdated platelets or saline preparations were transfused into the thrombocytopenic rabbits induced by doxorubicin. Hemostatic efficacy was demonstrated in all animals that received procoagulant membranes. Repeat measurements of bleeding time at 15 minutes, two and four hours post-transfusion showed a significant shortening of bleeding time from thrombocytopenic controls ($<0.01$) (FIG. 5). In contrast, no significant differences were noted between measurements obtained before and after infusion of saline to thrombocytopenic rabbits.

EXAMPLE 4

The efficacy of the platelet microparticles of the invention in controlling bleeding was further confirmed by the dose-dependant response when the microparticles were administered to severely thrombocytopenic rabbits. Two injections of busulfan (totalling 35 mg/kg body weight) were administered subcutaneously to rabbits to produce severe thrombocytopenia (platelet count less than 25,000 per ul). Three different doses of platelet microparticles (0.5 mg/kg body weight, 1.0 mg/kg body weight and 2.0 mg/kg body weight) and a saline control preparation were transfused into the severely thrombocytopenic rabbits. Baseline platelet counts determined on the day of transfusion for all animals was on the order of about 15,000/ul.

Figure 6:
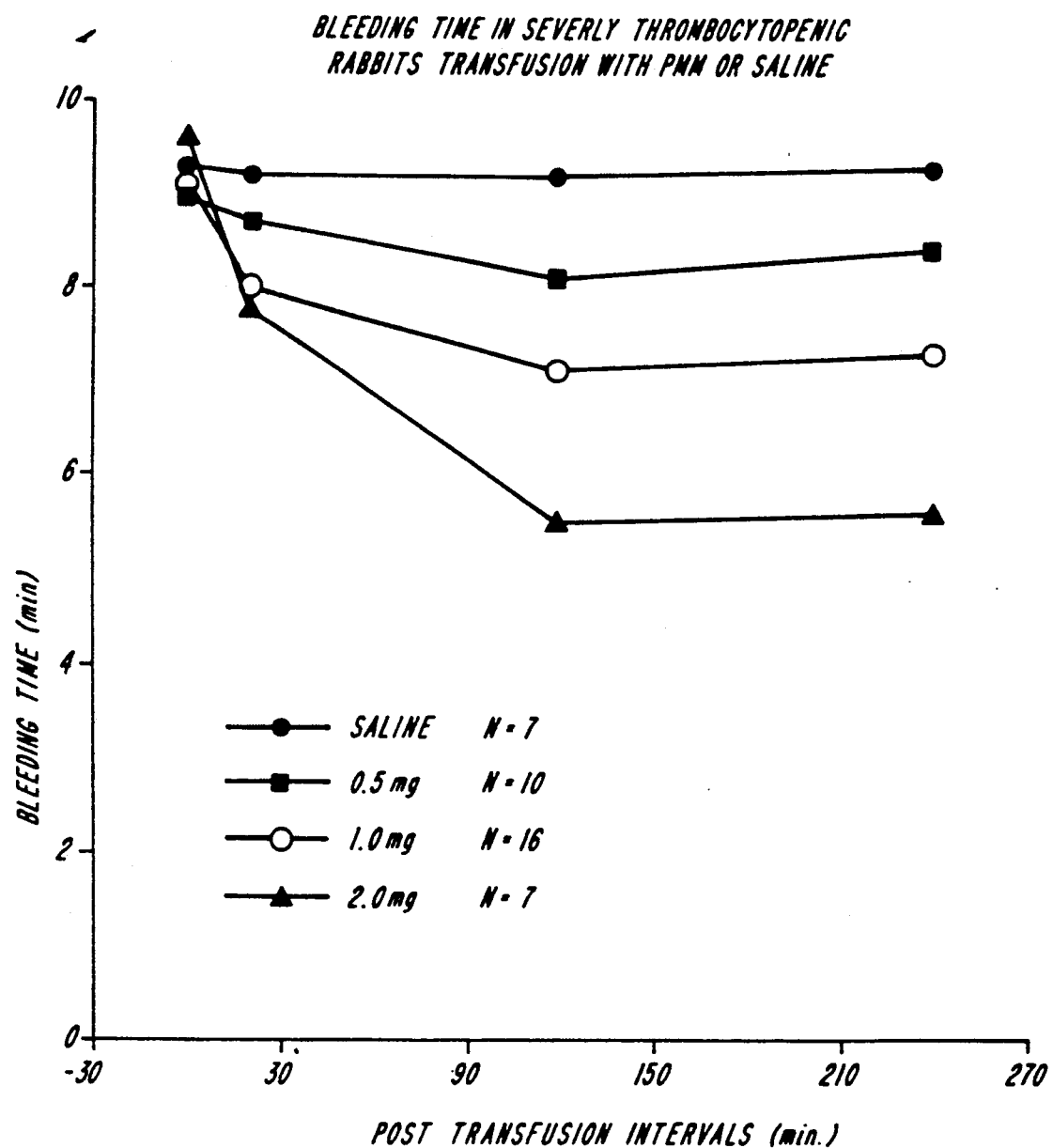
FIG. 6 is a graph showing the dose-dependant effect of transfused platelet membrane microparticles on the bleeding time and busulfan-induced, severely thrombocytopenic animals.

Referring to FIG. 6, the hemostatic efficacy of the platelet microparticles was directly related to the dose transfused. Transfusion of saline to the severely thrombocytopenic rabbits did not change the bleeding time. On the other hand, the prolonged bleeding time in severely thrombocytopenic rabbits was shortened in a dose-dependant manner when platelet microparticles were transfused.

The foregoing transfusion studies in thrombocytopenic rabbits demonstrate the hemostatic efficacy of the platelet membrane fragment preparation of the invention.

It will be understood by those skilled in the art that various changes and modifications to the embodiments shown in the drawings and described above may be made within the scope of the invention, It, therefore, is intended that all matter contained in the above description and shown in the accompanying drawings shall be interpreted in an illustrative and not limiting sense.

REFERENCES

1) Klein, E., Farber, S., Djersasi, I., Toch, R., Freeman, G., Arnold, P., "The Preparation and Clinical Administration of Lyophilized Platelet Material to Children with Acute Leukemia and Aplastic Anemia", *J. Pediatrics*, 49:517, 1956.
2) Hjort, P., Perman, V., and Cronkite, E., "Fresh, Disintegrated Platelets and Radiation Thrombocytopenia: Correction of Prothrombin Consumption without Correction of Bleeding".
3) McGill, M., Fugman, D., Vittorio, N., and Darrow, C., "Platelet Membrane Vesicles Reduced Microvascular Bleeding Times in Thrombocytopenic Rabbits", *J. Lab. Clin. Med*, 109:127-133, 1987.
4) Wu, V-Y., McCoy, L. E., "Platelet Factor 3: Quantitation and Characterization", *Thromb. Res.*, 11:581-593, 1977.
5) Spaet, T. H., Cintron, J., "Studies on Platelet Factor-3 Availability", *Brit. J. Hamematol*, 11:269, 1965.

What is claimed is:

1. A platelet membrane product derived from platelets of a mammalian species having a platelets comprising:
   isolated platelet membrane fragments that have procoagulant activity but are nonreactive with alloantibodies to HLA antigens of the species from which the platelets are derived.
2. The platelet membrane product as claimed in claim 1 wherein the isolated fragments are nonalloimmunogenic.
3. The platelet membrane product as claimed in claim 1 wherein the isolated fragment are nonimmunogenic.
4. The platelet membrane product as claimed in claim 1, 2 or 3 wherein the isolated fragments are free of GPIIb/IIIa activity.
5. The platelet membrane product as claimed in claim 1, 2 or 3 wherein the product is free of ghost platelets.
6. The platelet membrane product as claimed in claim 1, 2 or 3 wherein the isolated fragments are isolated microvesicles and said microversicles having a diameter left than 1 micron.
7. The platelet membrane product as claimed in claim 6 wherein the product is free of microvesicles having a diameter greater than 1 microns.
8. The platelet membrane product as claimed in claim 4 wherein the product is free of ghost platelets.
9. The platelet membrane product as claimed in claim 4 wherein the isolated fragments are isolated microvesicles and said microvesicles having a diameter less than 1 micron.
10. The platelet membrane product as claimed in claim 9 wherein the product is free of microvesicles having a diameter greater than 1 micron.
11. A platelet membrane product comprising
    isolated platelet membrane fragments that have procoagulant activity and that are free of GPIIb/IIIa complex.
12. The platelet membrane product as claimed in claim 11 wherein the product is free of ghost platelets.
13. The platelet membrane product as claimed in claim 11 wherein the isolated fragments are isolated microvesicles and said microvesicles having a diameter less than one micron.
14. The platelet membrane product as claimed in claim 13 wherein the product is free of microvesicles having a diameter greater than 1 microns.

* * * * *

UNITED STATES PATENT AND TRADEMARK OFFICE
CERTIFICATE OF CORRECTION

PATENT NO. : 5,332,578
DATED : July 26, 1994
INVENTOR(S) : Francis Chao

It is certified that error appears in the above-indentified patent and that said Letters Patent is hereby corrected as shown below:

Column 12, claim 1, line 18, delete "a" between "having" and "platelets".
         claim 7, line 40, delete "microns" and insert --micron--.
         claim 14, line 62, delete "microns" and insert --micron--.

Signed and Sealed this

Twenty-fourth Day of January, 1995

Attest:

BRUCE LEHMAN

Attesting Officer      Commissioner of Patents and Trademarks